United States Patent
Mikawa et al.

(10) Patent No.: US 6,600,056 B1
(45) Date of Patent: Jul. 29, 2003

(54) CATALYST FOR PRODUCTION OF EPOXIDES AND METHODS FOR PRODUCTION THEREOF AND EPOXIDES

(75) Inventors: Masatsugu Mikawa, Yokohama (JP); Shin-ichi Uchida, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 13 days.

(21) Appl. No.: 09/664,170

(22) Filed: Sep. 18, 2000

(30) Foreign Application Priority Data

Sep. 21, 1999 (JP) .......................................... 11-267467

(51) Int. Cl.$^7$ .......................................... C07D 301/10
(52) U.S. Cl. ...................................... 549/534; 549/536
(58) Field of Search ................................. 549/534, 536

(56) References Cited

U.S. PATENT DOCUMENTS

| | | | |
|---|---|---|---|
| 4,728,634 A | 3/1988 | Boxhoorn et al. | 502/243 |
| 4,897,498 A * | 1/1990 | Monnier et al. | 502/347 |
| 5,034,545 A | 7/1991 | Fischer | 549/507 |
| 5,081,096 A | 1/1992 | Monnier et al. | 502/348 |
| 5,138,077 A | 8/1992 | Monnier et al. | 549/536 |
| 6,313,325 B1 * | 11/2001 | Shima et al. | 549/534 |

FOREIGN PATENT DOCUMENTS

| | | | |
|---|---|---|---|
| EP | 0 318 815 A1 | 6/1989 | .......... C07D/301/10 |
| EP | 0 558 346 A1 | 9/1993 | ............ B01J/23/66 |
| EP | 0 927 575 A1 | 7/1999 | ............ B01J/23/66 |
| WO | WO 89/07101 | 8/1989 | .......... C07D/301/10 |
| WO | WO 93/03024 | 2/1993 | .......... C07D/301/10 |
| WO | WO 94/13653 | 6/1994 | .......... C07D/303/04 |
| WO | WO 97/40933 | 11/1997 | ............ B01J/23/66 |
| WO | WO 99/00188 | 1/1999 | ............ B01J/21/06 |

* cited by examiner

Primary Examiner—Ba K. Trinh
(74) Attorney, Agent, or Firm—Fish & Richardson P.C.

(57) ABSTRACT

It provide a catalyst for the production of epoxides by a vapor-phase oxidation of an unsaturated hydrocarbon having a chain length of 4–20 carbon atoms and containing no allylic hydrogen atom, characterized by having a catalytic component containing silver and at least one element selected from the group consisting of alkali metals and thallium deposited onto a carrier obtained by mixing $\alpha$-alumina having a sodium content in the range of 1–70 mmol (as reduced to Na) per kg of $\alpha$-alumina with an aluminium compound, a silicon compound, and a sodium compound and calcining the resultant mixture, the carrier having a silicon content (as reduced to $SiO_2$) in the range of 0.3–11.5 mass % based on the mass of the carrier and a sodium content (as reduced to $Na_2O$) in the range of 0.11–2.5 mass % based on the mass of the carrier.

12 Claims, No Drawings

CATALYST FOR PRODUCTION OF EPOXIDES AND METHODS FOR PRODUCTION THEREOF AND EPOXIDES

BACKGROUND OF THE INVENTION

1. Field of the Invention

This invention relates to a catalyst for the production of epoxides by catalytic vapor-phase oxidation of an unsaturated hydrocarbon having a carbon length of 4–20 carbon atoms and containing no allylic hydrogen atom with a molecular oxygen-containing gas thereby obtaining epoxides selectively in high yield.

2. Description of Related Art

Epoxide compounds are enable to use for extent. various reactions because of their high reactivity. For example 3,4-epoxy-1-butene which is one of epoxides of an unsaturated hydrocarbon having a carbon length of 4–20 carbon atoms and containing no allylic hydrogen atom, is an intermediate for the production of tetrahydrofuran (U.S. Pat. No. 5,034,545). Also the intermediate is used for a production of 1,2-butylene oxide (U.S. Pat. No. 5,034,545). It has been heretofore known that 3,4-epoxy-1-butene is produced by catalytic a vapor-phase oxidation of 1,3-butadiene with a molecular oxygen-containing gas in the presence of a catalyst. It has been also known that alumina, silicon and so on are used as the carrier thereof and an alkali metal and a thallium oxide are used as cationic components besides silver as catalyst component (WO89/07,101, WO93/03,024, U.S. Pat. No. 5,138,077, U.S. Pat. No. 5,081,096, and WO94/13,653).

These methods disclosed above, however, have the disadvantage that catalysts used therein possess low activity, exhibit low selectivity for 3,4-epoxy-1-butene, and suffer from a short catalyst life.

The catalysts for synthesizing epoxides include such catalysts as are obtained by depositing silver on porous inorganic carriers and used for the production of ethylene oxide. Among others there are silver-carried catalysts have been developed with a view to offering several years of service life on a commercial production. When these catalysts are used in the reaction for producing 3,4-epoxy-1-butene by the catalytic vapor-phase oxidation of 1,3-butadiene, they generally manifest substantially no catalytic activity or, if catalytically active at all, offer very short service lives as a catalyst. The epoxide of an unsaturated hydrocarbons having a chain length of 4–20 carbon atoms and containing no allylic hydrogen atom include such compounds as 3,4-epoxy-1-butene which need quantity production. For the catalysts to be effectively used in the reaction of a vapor-phase oxidation, it is an extremely important task for the sake of commercial production to enhance the performance of catalyst and elongate the service life of catalyst. Since the cause for degrading these catalysts remains yet to be elucidated, no effective method for solving this problem of degradation has been perfected so far.

SUMMARY OF THE INVENTION

An object of this invention, therefore, is to provide a novel catalyst for the production of epoxides by a vapor-phase oxidation of an unsaturated hydrocarbon having a carbon length of 4–20 carbon atoms and containing no allylic hydrogen atom.

Another object of this invention is to provide a method for manufacture of a catalyst for the production of epoxides having high activity, exhibiting high selectivity for epoxides, and enjoying a long catalyst life.

Further object of this invention is to provide a method of a catalyst for producing exoides.

Still another object of this invention is to provide a method for the production of 3,4-epoxy-1-butene in high yield by catalytic vapor-phase oxidation of 1,3-butadiene.

The objects mentioned above are accomplished by the following Items (1)–(4).

(1) A catalyst for the production of epoxides by a vapor-phase oxidation of an unsaturated hydrocarbon having a chain length of 4–20 carbon atoms and containing no allylic hydrogen atom, characterized by having a catalytic component containing silver and at least one element selected from the group consisting of alkali metals and thallium deposited onto a carrier obtained by mixing α-alumina having a sodium content in the range of 1–70 mmol (as reduced to Na) per kg of α-alumina with an aluminium compound, a silicon compound, and a sodium compound and calcining the resultant mixture, the carrier having a silicon content (as reduced to $SiO_2$) in the range of 0.3–11.5 mass % based on the mass of the carrier and a sodium content (as reduced to $Na_2O$) in the range of 0.11–2.5 mass % based on the mass of the carrier.

(2) A method for the preparation of a catalyst for the production of an epoxide by the vapor-phase oxidation of an unsaturated hydrocarbon having a chain length of 4–20 carbon atoms and containing no allylic hydrogen atom, characterized by causing a solution containing silver and at least one element selected from the group consisting of alkali metals and thallium to impregnate a carrier obtained by adding an aluminum compound, a silicon compound, and a sodium compound to α-alumina having a sodium content (as reduced to Na) in the range of 1–70 mmols per kg of the α-alumina and firing the resultant mixture and having a silicon content (as reduced to $SiO_2$) in the range of 0.3–11.5 mass % per mass of the carrier and a sodium content (as reduced to $Na_2O$) in the range of 0.11–2.5 mass % per mass of the carrier.

(3) A method for the production of epoxides, which comprises effecting said production by a vapor-phase oxidation of an unsaturated hydrocarbon having a chain length of 4–20 carbon atoms and containing no allylic hydrogen atom with a molecular oxygen-containing gas in the presence of a catalyst set forth in Item (1).

(4) A method for the production of 3,4-epoxy-1-butene, which comprising effecting said production by a vapor-phase oxidation of 1,3-butadiene with a molecular oxygen-containing gas in the presence of a catalyst set forth in Item (1).

The catalyst of this invention, owing to the construction thereof described above, excels in activity and selectivity for epoxide and enjoys a long life time. The use of this catalyst allows epoxide to be produced with high productivity by catalytic vapor-phase oxidation of unsaturated hydrocarbon. The above and other objects, features and advantages of the present invention will become clear from the following description of the preferred embodiments.

DESCRIPTION OF THE PREFERRED EMBODIMENTS

The first aspect of this invention concerns a catalyst for the production of epoxides by a vapor-phase oxidation of an unsaturated hydrocarbon having a chain length of 4–20 carbon atoms and containing no allylic hydrogen atom, characterized by having a catalytic component containing silver and at least one element selected from the group consisting of alkali metals and thallium deposited onto a carrier obtained by mixing α-alumina having a sodium content in the range of 1–70 mmol (as reduced to Na) per kg of α-alumina with an aluminium compound, a silicon compound, and a sodium compound and calcining the resultant mixture, the carrier having a silicon content (as reduced to SiO$_2$) in the range of 0.3–11.5 mass % based on the mass of the carrier and a sodium content (as reduced to Na$_2$O) in the range of 0.11–2.5 mass % based on the mass of the carrier.

The unsaturated hydrocarbon contemplated by this invention is only required to be a compound which has a chain length of 4–20 carbon atoms and containing no allylic hydrogen atom. The term "allylic hydrogen" as used in this invention means the two hydrogen atoms which are bound to the carbon atoms adjoining the double bond of an allyl group represented by the formula, CH$_2$=CH—CH$_2$— and the expression "containing no allylic hydrogen" means that at least one of the two hydrogen atoms mentioned above is absent.

To be specific, the compound in question is represented by the following formula.

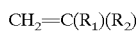

$$CH_2=C(R_1)(R_2)$$

(wherein R$_1$ denotes a hydrogen atom or an alkyl group, R$_2$ denotes an aryl group or a tertiary alkyl group or —C(R$_3$)=CH$_2$, and R$_3$ denotes a hydrogen atom or an alkyl group.)

The term "chain length" as used herein is to be interpreted as embracing not only a chain optionally containing a branch but also a ring. The alkyl groups denoted by R$_1$ and R$_3$ are independently methyl group, ethyl group, butyl group, heptyl group, octyl group, etc. Then, R$_2$ is t-butyl group, phenyl group, etc.

The unsaturated hydrocarbon having a chain length of 4–20 carbon atoms and containing no allylic hydrogen atom and forming the target for this invention is an unsaturated hydrocarbon having a chain length preferably in the range of 4–12, more preferably in the range of 4–8 carbon atoms and containing no allylic hydrogen. As concrete examples of the unsaturated hydrocarbon of interest, such compounds as 1,3-butadiene, tertiary butyl ethylene, and styrene may be cited. In this invention, it is advantageous to use 1,3-butadiene or tertiary butyl ethylene. In consideration of the convenience of explanation, the production of 3,4-epoxy-1-butene by the catalytic a vapor-phase oxidation of 1,3-butadiene will be described as a typical example.

The catalyst of the present invention for the production of epoxides, as described above comprises catalyst components silver and at least one element selected from the group consisting of alkali metals and thallium and a carrier thereof for depositing these elements. The carrier to be deposited catalytic components comprises mainly α-alumina. The α-alumina to be used in the present invention imposes no particularly restriction except for having a sodium content in the range of 1–70 mmol (as reduced to Na) per kg of α-alumina. The α-alumina to be on the market is available in this invention.

If the sodium content is less than 1 mmol/kg, the shortage will be at a disadvantage in lowering the selectivity. Conversely, if the sodium content exceeds 70 mmols/kg, the excess will be at a disadvantage in degrading both the degree of conversion and the selectivity without bringing a proportionate addition to the catalytic activity. That is, the present invention is enabled, by using α-alumina having a sodium content in the range of 1–70 mmols/kg, to secure the stability of α-alumina as a carrier and, by allowing the α-alumina to contain sodium in an amount in the specific range, to acquire exceptionally outstanding selectivity and degree of conversion as well. The fact that by varying the sodium content in the carrier as described above, the catalyst for oxidizing a hydrocarbon compound having a chain length of 4–20 carbon atoms and containing no allylic hydrogen atom is enabled to acquire excellent selectivity and degree of conversion has never been known to the art to date. Particularly in the catalyst of this invention for the production of an epoxide, since the α-alumina is mixed with a sodium compound and then calcined, the carrier never fails to incorporate therein a sodium component besides the sodium inherently present in the α-alumina. It has been ascertained that notwithstanding the complete carrier has a fixed sodium content, the carrier is deficient in either the selectivity or the degree of conversion when the sodium content (as reduced to Na) in the α-alumina itself deviates from the range of 1–70 mmols/kg. Though the reason for this peculiar mechanism is not clear, the mechanism may be logically explained by a supposition that the catalyst manifests an excellent catalytic activity when it incorporates therein sodium or a sodium compound in a specific amount.

The carrier to be used in the present invention is obtained by mixing α-alumina mentioned above with at least an aluminium compound, a silicon compound and a sodium compound, further an organic binder and a pore forming agent and calcining them, the silicon content (converted into SiO$_2$) is in the range of 0.3–11.5 mass % based on the mass of the carrier, more preferably 0.5–11 mass %, and most preferably 0.5–10 mass %. If the silicon content is less than this limit, the amount of acid on the surface of the carrier will be unduly small and the effect due to the acidity of the surface will manifest with difficulty.

In contrast, if the silicon content exceeds-this limit, the surface area of the carrier will not be controlled easily.

The content of the aluminium compound which is added into α-alumina except α-alumina itself imposes no restriction particularly, but preferably in the range of 0.1–20 mass % based on the mass of the carrier, more preferably 0.5–15 mass %, and most preferably 1–10 mass %. If the aluminium content exceeds this limit, the excess will be at a disadvantage in degrading the selectivity.

On the other hand, the sodium content of the carrier is in the range of 0.11–2.5 mass % based on the mass of the carrier, more preferably 0.11–2.3 mass %, and most preferably 0.11–2.0 mass %.

If the content of a sodium compound is less than 0.11 mass %, the shortage will be at a disadvantage in degrading the strength of the carrier during the reaction of oxidation of an unsaturated hydrocarbon having a chain length of 4–20 carbon atoms and containing no allylic hydrogen atom and impairing the selectivity and the degree of conversion as well. Conversely, if the content exceeds 2.5 mass %, the excess will be at a disadvantage in degrading both the selectivity and the degree of conversion. This invention, by limiting the content of a sodium compound in the carrier to the range mentioned above in the reaction of oxidation of an unsaturated hydrocarbon having a chain length of 4–20 carbon atoms and containing no allylic hydrogen atom, is enabled to acquire an effect of producing a catalyst having a long service life and excelling in both the selectivity and the degree of conversion as well.

Further, the silicon (as reduced to SiO$_2$) content per unit surface area of the carrier is in the range of 0.1–20 mass %/(m$^2$/g), preferably 0.15–18 mass %/(m$^2$/g), and most preferably 0.2–15 mass %/(m²/g). If the content of silicon is less than 0.1 mass %, the shortage will be at disadvantage in suffering the catalyst to manifest an inferior initial performance and an inferior strength in the reaction of oxidation of a hydrocarbon compound having a chain length of 4–20 carbon atoms and containing no allylic hydrogen atom. Conversely, if this content exceeds 20 mass %, the excess will be at a disadvantage in compelling the catalyst to suffer such a large decline in the selectivity, resulting in ineffective. This invention has originated in the discovery that, by limiting the content of silicon in the carrier to the aforementioned range in the reaction of oxidation of an unsaturated hydrocarbon having a chain length of 4–20 carbon atoms and containing no allylic hydrogen atom, it is made possible to secure the physical strength of the carrier and elongate the service life of the catalyst as well.

The mass ratio of silicon to sodium in the carrier ($SiO_2$/$Na_2O$) is in the range of 1–20, more preferably 2–20, and most preferably 3–18.

As mentioned above, the sodium compound content (as reduced to $Na_2O$) in the carrier, the amount of silicon (as reduced to $SiO_2$) per unit surface area, and the mass ratio of silicon (as reduced to $SiO_2$) to sodium compound (as reduced to $Na_2O$) are important factors which may be depended on by chemical property of the surface of the carrier (the acidity and basicity) and physical property of the carrier itself. If the sodium content is unduly low, the strength of the carrier will be degraded. The sodium content may depend on the amount of silicon in the carrier. If the sodium content is unduly large, the surface acidity will be lost, and the produced catalyst will be deficient in initial performance and in catalyst life as well. In the reaction of oxidation of a hydrocarbon compound having a chain length of 4–20 carbon atoms and containing no allylic hydrogen atom, the initial performance of the catalyst reflects the degree of conversion of the hydrocarbon compound and the selectivity of the epoxide at a specific reaction temperature after the start of the reaction. The decline of the catalyst performance represented by the degree of conversion manifests in the form of a decrease in either or both of the degree of conversion am and the selectivity and brings about harm.

Incidentally, the carrier is confirmed by the X-ray diffraction analysis to have formed $Al_6Si_2O_{13}$ originating in the silica component besides the a-$Al_2O_3$. The presence of this $Al_6Si_2O_{13}$ is believed to bring an influence on the manifestation of the acidity of the surface of the produced carrier. When this carrier was tested for acidity, it showed such acidity as detectable with an indicator (methyl red) of pKa +4.8. From this fact, it is inferred that the carrier used in this invention is enabled, by mixing an aluminum compound, a silicon, and a sodium compound and calcining the resultant mixture, to manifest eventually such acidity as detectable with an indicator of pKa +4.8 and further that the catalyst is enabled, by causing the carrier to bring a synergistic effect with a catalytic component, i.e. such a cation component as at least one element selected from the group consisting of alkali metals and thallium, to manifest an exceptionally high catalytic performance.

In order that the carrier used in this invention may enable the catalyst for the production of epoxide contemplated by this invention to acquire an ability to repress sequential oxidation, for example, due to the stagnation in the micropores in the catalyst of the product (such as, for example, 3,4-epoxy-1-butene) of the oxidation of an unsaturated hydrocarbon having a chain length of 4–20 carbon atoms and containing no allylic hydrogen atom by the use of the catalyst of this invention and exhibit high selectivity, the amount of the micropores constitutes itself an important factor. It is particularly important to control the formation of micropores in the catalyst so that the volume ratio of pores having diameters of not more than 0.5 μm is not more than 50%, more preferably not more than 45%, and most preferably not more than 40% and the volume ratio of the pores having diameters of not more than 5 μm exceeds 65%, more preferably exceeds 70%. Particularly, when the raw material compound is a hydrocarbon compound having a chain length of 4–20 carbon atoms and containing no allylic hydrogen atom, the carrier prefers copious presence therein of micropores having diameters of 0.5–5 μm. If the volume ratio of pores having diameters of not more than 0.5 μm exceeds 50%, the excess will induce formation of the by-product by the sequential reaction and degrade the selectivity. Conversely, if the volume ratio of the pores having diameters exceeding 5 μm in the carrier exceeds 65%, the excess will be at a disadvantage in degrading the selectivity and the grade of conversion due to the absence of the retention of the raw material compound in the pores of the catalyst and preventing the catalyst from attaining an extension of the service life thereof.

The specific surface area of the carrier is in the range of 0.1–5 m²/g, more preferably 0.3–3 m²/g, and most preferably 0.5–3 m²/g. It is difficult to produce a catalyst with sufficient strength when using a carrier which has a surface area of more than 5 m²/g, and such catalyst has only a low selectivity. In terms of catalyst life, it is important that the sufficient amount of silver in the form of fine particle is supported on the carrier. It is difficult to produce a catalyst having both of above-mentioned factors when using the carrier having a surface area of less than 0.1 m²/g.

The water absorption ratio of the carrier is in the range of 20–50%, more preferably 25–50%, and most preferably 30–45%. If this absorption ratio is less than 20%, it will be difficult to deposit the prescribed amount of silver on the carrier. Conversely, if this water absorption ratio exceeds 50%, the carrier will be deficient in terms of strength at all.

The second aspect of this invention concerns a method for the preparation of a catalyst for the production of an epoxide by the vapor-phase oxidation of an unsaturated hydrocarbon having a chain length of 4–20 carbon atoms and containing no allylic hydrogen atom, characterized by causing a solution containing silver and at least one element selected from the group consisting of alkali metals and thallium to impregnate a carrier obtained by adding an aluminum compound, a silicon compound, and a sodium compound to α-alumina having a sodium content (as reduced to Na) in the range of 1–70 mmols per kg of the α-alumina and firing the resultant mixture and having a silicon content (as reduced to $SiO_2$) in the range of 0.3–11.5 mass % per mass of the carrier and a sodium content (as reduced to $Na_2O$) in the range of 0.11–2.5 mass % per mass of the carrier.

The carrier to be used in the invention may be prepared, for example, by the following method. After α-alumina powder mentioned above is mixed with water, an aluminium compound, silicon and a sodium compound, then added an organic binder. The obtained composition is mixed and formed according to designated form and measurement. After drying it, it is calcined at a temperature in the range of 1,100–1,700° C., preferably 1,150–1,600° C.

As the α-alumina powder to be used in the present invention, α-alumina secondary particles which have a diameter in the range of 20–200 μm, preferably 25–100 μm and have a specific surface area thereof in the range of 0.1–20 m²/g, preferably 0.3–15 m²/g, may be used in the present invention, wherein the secondary particles are composed by alumina primary particles having a diameter in the range of 0.1–10 μm, preferably 1–7 μm. The sizes of the primary particles and the secondary particles of the raw material α-alumina powder bring an influence to bear on the pore distribution in the completed carrier. The pore distribution of the carrier is particularly preferred to be such that the volume ratio of the pores having diameters of not more than 0.5 μm is not more than 50% and the volume ratio of the pores having diameters of not more than 5 μm is not less than 65%. By using α-alumina formed of the secondary particles mentioned above, it is made possible to obtain readily a carrier having a pore distribution in the range mentioned above.

In the present invention, an aluminium compound to be mixed with α-alumina includes aluminium oxides such as β-alumina, γ-alumina, hydroxides such as gibbsite and boehmite, aluminium salts such as aluminum nitrate and aluminium sulfate and alminium compound to be oxide by calcining with α-alumina particle, but except α-alumina itself. Among them, colloidal-alumina such as an aluminasol may be used as aluminium compound.

In addition of colloidal-silica, as typical example of the silicon compound mentioned above, covalent bond compound such as silicon oxide, silicon nitride, silicon carbide, silane, and silicon sulfate; silicates such as sodium silicate, ammonium silicate, sodium alumino-sulicate, ammonium aluminosilicate, sodium phosphosilicate, and ammonium phosphosilicate; complex salts of silica containing such silicon as feldspar and clay; and silica mixture may be cited.

Furthermore, clay mineral such as silica-alumina, mullite and zeolite may be used as aluminium compound and silicon compound.

As typical example of the sodium compound mentioned above, inorganic salts such as sodium nitrate, sodium carbonate, sodium bicarbonate, sodium chloride, sodium fluoride, sodium nitrite, sodium sulfate; carboxylates such as sodium formate and sodium acetate; and sodium hydroxide may be cited.

Sodium component can be introduced to the α-alumina in any way, for example, introduced as a component of organic binder and/or inorganic binder and/or sodium-enriched alumina calcined a mixture of sodium salt and alumina compounds. Any means can be employed to add the sodium to the carrier in the carrier preparation in this invention.

As typical example of the organic binder mentioned above, methylcellulose, hydroxymethycellulose, carboxylmethycellulose, corn starch and so on may be cited.

As the pore forming agents, particles of walnut seed shell, particles of peach seed, polymers and so on having the same particle diameter as α-alumina may be cited.

The carrier to be used in this invention can be prepared by any of the methods heretofore known to the art. One method, for example, attains the preparation by kneading the α-alumina powder with methyl cellulose added thereto as an organic binder, adding to the resultant mixture granular alumina sol, colloidal-silica, and further sodium hydroxide, and mixing the produced mixture with water added thereto. The final mixture is extrusion molded, then granulated, dried, and subsequently fired. Though the calcining temperature does not need to be particularly limited, the calcining is carried out at a temperature in the range of 1000–1700° C., preferably in the range of 1300–1500° C. The calcining time is in the range of 0.5–5 hours, preferably 1–3 hours. By boiling to clean the granular product in boiling water several times, the carrier aimed at can be obtained.

The silver compound to be used for the formation of silver as a catalytic component of the catalyst of this invention is only required to be capable of forming a complex with amine, soluble in an aqueous solvent and decomposing to separate silver at a temperature of not higher than 500° C., preferably not higher than 300° C., and more preferably not higher than 260° C. As typical examples of the silver compound which answers the description, silver oxide, silver nitrate, silver carbonate and various silver carboxylates such as silver acetate and silver oxalate may be cited. Among other silver compounds mentioned above, silver oxalate proves to be particularly advantageous. The amine as a complexing agent imposes no restriction particularly but requires only to be capable of dissolving the silver compound mentioned above in an aqueous solvent. Pyridine, acetonitrile, ammonia, and amines of 1–6 carbon atoms are concrete examples of the amine of this description. Among them, ammonia, monoamines such as pyridine and butyl amine, alkanol amines such as ethanol amine, alkylene diamines of 2–4 carbon atoms, and polyamines prove to be particularly advantageous. It is particularly preferable to use ethylene diamine and ethanol amine, either singly or in the form of a mixture.

In this case, the ratio of the amounts of the silver compound and amine to be mixed is properly in the range of 1–2 mols of amine, preferably in the range of 1–1.5 mols of amine, per mol of the silver compound. In this case, when a plurality of kinds of silver compound and amine are used, the mol numbers mentioned above apply to the totals of the kinds of compounds.

For the purpose of depositing silver on the carrier, it is most realistic to use the silver compound and the amine in the form of aqueous solutions thereof. Optionally, water-based solutions of the silver compound and the amine which incorporate an alcohol therein may be used. The silver concentration in the aqueous solution is selected so that the silver as the catalyst component is eventually deposited in an amount in the range of 5–25 mass %, preferably 5–20 mass %, based on the total mass of the catalyst.

The impregnation to support silver to the carrier is carried out by well known method in the prior art. Such operations as reducing pressure, application of heat, spraying the solution to the carrier and combination thereof are performed, if necessary. The amine is added in an amount necessary for forming a complex of the silver compound. Generally it raises a reproducibility of catalyst preparation by adding in an amount of 5–30% in excess of the equivalent weight. Heat treatment following to the impregnation is performed at a temperature and time necessary for deposition of silver on the carrier. It is most preferable to select the condition so that silver particles is deposited on the carrier as uniform and minute as possible. A high temperature and/or a long duration for the heat treatment are generally unfavorable because they are liable to promote sintering of silver particles. It is preferred method, therefore, that the impregnated catalyst is treated with air (or an inert gas such as nitrogen) preheated to a temperature in the range of 120° C.–450° C. or superheated steam for a short duration of 5–60 minutes. The brief treatment just mentioned is also advantageous from the viewpoint of curtailing the time for the process of preparation of the catalyst.

The at least one element selected from the group consisting of alkali metals and thallium and deposited as a catalytic component is preferred to be in the form of a compound soluble in a water-based solvent and is used in a wholly dissolved state. Part of the catalytic component may be in a partly undissolved state. The compounds which answer this description include nitrates, carbonates, bicarbonates, halogen salts, nitrites, sulfates, and other inorganic salts, formates and other carboxylates, and hydroxides of thallium and alkali metals such as lithium, sodium, potassium, rubidium, cesium, and francium, for example. As more concrete examples of these compounds, cesium nitrate, cesium hydroxide, cesium chloride, cesium carbonate, cesium sulfate, lithium nitrate, lithium hydroxide, lithium chloride, lithium carbonate, lithium oxalate, lithium sulfate, lithium borate, sodium nitrate, sodium carbonate, sodium bicarbonate, sodium acetate, sodium borate, sodium ethoxide, potassium nitrate, rubidium nitrate, thallium chloride, thallic nitrate, thallium sulfate, thallium carbonate, and thallium oxalate may be cited.

The catalyst for the production of an epoxide contemplated by the present invention may incorporate therein other metal. The metals usable for this incorporation include alkaline earth metals such as magnesium, calcium, strontium, and barium, rare earth metals such as scandium, yttrium, cerium, lanthanum, neodymium, praseodymium, and europium, metals such as copper, gold, lead, cadmium, titanium, zirconium, hafnium, germanium, tin, vanadium, niobium, tantalum, phosphorus, arsenic, antimony, bismuth, chromium, and molybdenum, and other elements. These metals may be used either singly or in the form of a combination of two or more members. As concrete compounds which can be arbitrarily incorporated, magnesium nitrate, magnesium carbonate, magnesium oxalate, magnesium ethoxide, calcium nitrate, calcium hydroxide, calcium chloride, calcium acetate, calcium sulfate, calcium molybdate, barium nitrate, strontium nitrate, strontium hydroxide, strontium chloride, yttrium nitrate, yttrium chloride, yttrium carbonate, yttrium oxalate, yttrium acetate, cerium nitrate, cerium hydroxide, cerium carbonate, cerium sulfate, lanthanum nitrate, neodymium nitrate, praseodymium nitrate, europium nitrate, copper nitrate, copper hydroxide, copper carbonate, copper oxalate, copper acetate, copper sulfate, copper borate, copper molybdate, lithium tetrachloroaurate, sodium tetrachloroaurate, zinc nitrate, zinc chloride, zinc carbonate, zinc nitrate, zinc acetate, zinc borate, zinc chlorate, zinc molybdate, cadmium nitrate, cadmium hydroxide, mercurous nitrate, mercurous sulfate, ammonium borate, potassium borate, gallium hydroxide, gallium chloride, indium nitrate, indium chloride, indium sulfate, tetraisopropoxy titanium, zirconium nitrate, zirconium hydroxide, zirconium hydrochloride, zirconium sulfate, hafnium chloride, lithium zirconate, sodium zirconate, ethyl silicate, lithium germanate, sodium germanate, potassium germanate, tin chloride, tin acetate, lithium stannate, potassium stannate, lead nitrate, lead hydroxide, vanadium chloride, sodium vanadate, potassium vanadate, niobium oxalate, potassium niobate, tantalum hydroxide, tantalum chloride, tantal isopropoxide, sodium tantalate, potassium tantalate, ammonium phosphate, sodium phsophate, potassium phosphate, sodium hydrogen phosphate, potassium hydrogen phosphate, strontium hydrogen phosphate, arsenic chloride, antimony chloride, antimony tartrate, antimony sulfate, bismuth nitrate, bismuth chloride, bismuth sulfate, tellurium chloride, ammonium tellurate, sodium tellurate, lithium tellurite, sodium tellurite, sodium chromate, lithium chromate, and lithium molybdate may be cited.

These elements may be deposited (and simultaneously used for impregnation) as incorporated in an aqueous silver solution. They may be deposited prior to the deposition of silver (referred to as "preimpregnation") or subsequently to the deposition of silver (referred to as "afterimpregnation"). For the afterimpregnation, the elements are used in the form of an aqueous solution. Optionally, the deposition may be accomplished by dissolving the elements in an alcohol, for example, immersing in the resultant solution a carrier having silver deposited thereon in advance, stripping the impregnated carrier of the excess solution, and then drying the resultant wet carrier.

The silver catalyst of this invention properly contains silver in an amount in the range of 5–25 mass %, based on the total mass of the catalyst and, at the same time, contains at least one element selected from the group consisting of thallium and alkali metals in an amount in the range of 0.001–5 mass %, preferably in the range of 0.005–3 mass %, and particularly preferably in the range of 0.01–0.2 mass %, based on the mass of the catalyst. As the alkali metal to be deposited in the catalyst of this invention, sodium, potassium, rubidium, and/or cesium prove particularly advantageous among other alkali metals mentioned above. When the amount of the alkali metal to be deposited is in the range of 0.001–5 mass %, the catalyst of this invention does not need to contain thallium. The catalyst, however, may contain thallium in conjunction with the alkali metal. The amount of potassium to be deposited is particularly preferred to be in the range of 0.01–0.8 mass %, that of rubidium to be in the range of 0.02–1.0 mass %, that of cesium to be in the range of 0.01–2 mass %, and that of thallium in the range of 0.001–2 mass % respectively. If the amount of an alkali metal or thallium to be deposited in the catalyst falls short of 0.001 mass %, the shortage will possibly lower the selectivity conspicuously, curtail the service life of the catalyst, and entail extinction of the catalytic activity during a protracted use even where the other requirements of the carrier are fulfilled. Conversely, if the amount exceeds 5 mass %, the excess will be at a disadvantage in enlarging the degree of conversion particularly. Such catalytic components are deposited most advantageously simultaneously with the silver. Commendably, these catalytic components are added partly or wholly in the form of halogenides such as chlorides, bromides, or fluorides or nitrates or sulfates.

In the method for depositing the cation component mentioned above by the operation of preimpregnation or afterimpregnation, when the cation component is added in the form of an aqueous solution, the deposition is preferred to be attained by drying the aqueous solution with air heated to 110–200° C. for a period in the range of 5–60 minutes. Superheated steam may be used in the place of the air in this drying operation. When an alcohol such as ethyl alcohol is added as the solvent, the deposition is preferred to be effected by drying the solution with an inert gas such as air or nitrogen heated to a temperature not higher than 100° C., preferably not higher than 50° C. Consequently, the cation component is uniformly dispersed on the carrier.

As the method for heating the catalyst with air or the inert gas such nitrogen or with the superheated steam in this invention, the catalyst may be piled in a single layer or a plurality of layers in the form of a fixed bed or a moving bed and the inert gas such as air or nitrogen or the superheated steam may be passed through this bed downward, upward, or sideward. The duration of this treatment may be properly selected to suit the temperature and the flow rate of the air or inert gas such as nitrogen or the superheated steam. As respects the flow rate, the treatment at a flow rate in the range of 0.3–1 m/second where the catalyst is treated in a single layer or a plurality of layers as in the mesh-belt drying device or at a flow rate in the range of 0.7–3 m/second where the catalyst is treated in a tube having a large bed length as in the shell-and-tube type reaction vessel proves economical from the practical point of view because of the absence of uneven silver distribution in the catalyst. When the superheated steam is used, it may incorporate therein nitrogen or air to a certain extent.

This invention prefers depositing the catalyst component containing silver and at least one element elected from the group consisting of alkali metals and hallium on the carrier mentioned above and thereafter heat-treating the resultant composite finally at an elevated temperature in the range of 400–700° C. in an inert gas containing substantially no oxygen. The silver catalyst of this invention serves the purpose of effecting gas phase oxidation of an unsaturated hydrocarbon having a chain length of 4–20 carbon atoms and containing no allylic hydrogen atom. Since this catalyst has a short service life and consequently requires such a procedure as suspending the operation of the apparatus and packing the apparatus with a fresh supply of the catalyst, the productivity of the epoxide is degraded. It is believed that this invention is enabled to stabilize the silver, alkali metal, thallium, etc. deposited on the carrier by performing in advance the heat treatment at the elevated temperature in the inert gas for some unaccountable reason. It is considered that the selectivity is maintained particularly in consequence of repressing the rise of the reaction temperature during a protracted use of the catalyst. In fact, by the treatment mentioned above, the selectivity and the degree of conversion can be secured stably from the start of the use of the catalyst onward and, moreover, the service life of the catalyst can be elongated.

The expression "the inert gas containing substantially no oxygen" as used herein means one member or a mixture of two or more members selected from the group consisting of nitrogen, helium, argon, carbon dioxide, and neon. Among other inert gases enumerated above, nitrogen proves particularly advantageous because it is inexpensive and easy to procure. Then, the term "substantially" used in the preceding expression means that oxygen may be contained to the extent of bringing no adverse effect on the property of oxidation, preferably up to not more than 3 vol. % in concentration. Though the reason for necessitating substantial absence of oxygen is not clear, this necessity may be logically explained by a supposition that when the heat treatment at the elevated temperature proceeds in the presence of oxygen, the deposited silver gains so much in particle diameter after this heat treatment possibly as to degrade the catalytic activity and curtail the service life of the catalyst. When the heat treatment is performed in the state containing "substantially" no oxygen, therefore, the silver shows virtually no change in particle diameter before and after the treatment. Consequently, the thermostablity can be improved thereby the stable catalytic activity can be attained in conjunction with the elongation of the service life of the catalyst.

The expression "the heat treatment at an elevated temperature" as used herein refers to a heating operation performed at a temperature in the range of 400–700° C., preferably 450–650° C. If this temperature falls short of 400° C., the aforementioned effect of elongating the service life of the catalyst will fail to manifest and the heat treatment at the elevated temperature will require a long time. Conversely, if this temperature exceeds 700° C., the excess will possibly bring a decrease in the selectivity. The pressure in this treatment does not need to be particularly specified. The temperature of the heat treatment, the duration of the treatment, and the concentration of oxygen constitute themselves the important factors.

The duration of the heat treatment at the elevated temperature is in the range of 5 minutes–30 hours, preferably 30 minutes–20 hours, and particularly preferably 30 minutes–10 hours.

The heat treatment at the elevated temperature, for the purpose of imparting activity to the silver compound and the other metal component deposited on the carrier, is performed after the catalytic component has been deposited on the carrier.

In the catalyst which has undergone the heat treatment at the elevated temperature as described above, the catalytic component deposited on the produced catalyst is preferred to contain silver in an amount in the range of 5–25 mass % based on the mass of the catalyst and, at the same time, contain the at least one element selected from the group consisting of thallium and alkali metals in an amount in the range of 0.001–5 mass %, preferably 0.005–3 mass %, and particularly preferably 0.01–2 mass %, based on the mass of the catalyst. As the alkali metal to be deposited in the catalyst of this invention, sodium, potassium, rubidium, and/or cesium prove particularly advantageous among other alkali metals mentioned above. When the amount of the alkali metal to be deposited is in the range of 0.001–5 mass %, the catalyst of this invention does not need to contain thallium. The catalyst, however, may contain thallium in conjunction with the alkali metal. The amount of potassium to be deposited is particularly preferred to be in the range of 0.01–0.8 mass %, that of rubidium to be in the range of 0.02–1.0 mass %, that of cesium to be in the range of 0.01–2 mass %, and that of thallium in the range of 0.01–2 mass % respectively. If the amount of an alkali metal or thallium to be deposited in the catalyst falls short of 0.001 mass %, the shortage will possibly lower the selectivity conspicuously, curtail the service life of the catalyst, and entail extinction of the catalytic activity during a protracted use even where the other requirements of the carrier are fulfilled. Conversely, if the amount exceeds 5 mass %, the excess will be at a disadvantage in enlarging the degree of conversion particularly.

The catalyst and the carrier are preferred to be shaped in the form of spheres, pellets, or rings measuring in the approximate range of 3–12 mm, particularly 4–10 mm.

The third aspect of this invention concerns a method for the production of epoxides, which comprises effecting said production by the vapor-phase oxidation of an unsaturated hydrocarbon having a chain length of 4–20 carbon atoms and containing no allylic hydrogen atom with a molecular oxygen-containing gas in the presence of the catalyst of this invention described above.

The compound having a chain length of 4–20 carbon atoms and containing no allylic hydrogen atom and used as the raw material herein is an unsaturated hydrocarbon which has a chain length preferably of 4–12, more preferably 4–8 carbon atoms and contains no allylic hydrogen atom as mentioned above. As concrete examples of the compound which answers the description, 1,3-butadiene, tertiary butyl ethylene, and styrene may be cited. This invention particularly prefers using 1,3-butadiene or tertiary butyl ethylene. The catalyst of this invention for the production of an epoxide is intended to catalyze a vapor-phase oxidation. For the purpose of enabling the reaction of oxidation to proceed in gas phase on the surface of the catalyst, this catalyst is preferred to use as the target thereof a compound having a low boiling point from the standpoint of the service life of catalyst.

For this reaction of oxidation, any of the known reaction vessels which are effectively applicable to the reaction of gas phase oxidation of an unsaturated hydrocarbon having a chain length of 4–20 carbon atoms and containing no allylic hydrogen atom can be adopted.

To be specific, the total pressure of the feed raw material containing an unsaturated hydrocarbon having a chain length of 4–20 carbon atoms and containing no allylic hydrogen atom, a molecular oxygen-containing gas, and a diluent gas and a reaction adjusting agent which will be described more specifically below is in the range of 0.01–10 MPa, preferably 0.01–4 MPa, and more preferably 0.02–3 MPa. The molar ratio of the unsaturated hydrocarbon having a chain length of 4–20 carbon atoms and containing no allylic hydrogen atom to 1 mol of oxygen is in the range of 0.001–100, preferably 0.01–50.

To the reaction vessel which is packed with the catalyst of this invention, a mixture of a molecular oxygen-containing gas, an unsaturated hydrocarbon having a chain length of 4–20 carbon atoms and containing no allylic hydrogen atom, and one or more diluent gases selected from among nitrogen, helium, argon, carbon dioxide, and alkane may be supplied. The partial pressures of these gas components being supplied to the reaction vessel must be selected so as to form a gas composition deviating from explosion limits in the reaction vessel.

The raw material gas may incorporate therein a reaction adjusting agent. The reaction adjusting agent is a compound containing a halogen. As concrete examples of the compound, chlorinated alkenes of 1–6 carbon atoms such as chlorinated ethylene, vinyl chloride, methyl chloride, and t-butyl chloride; chlorinated benzenes such as dichloromethane, dichloroethylene, trichloroethylene, chloroform, chlorinated biphenyl, and monochlorobenzene; brominated alkenes of 1–6 carbon atoms such as dichloropropane, dibromopropane, dichloropropene, dibromopropene, chlorobutane, bromobutane, dichlorobutane, dibromobutane, chlorobutene, dibromoethylene, tribromoethylene, brominated ethylene, vinyl bromide, methyl bromide, and t-butyl bromide; and brominated benzenes such as dibromomethane, tetrabromomethane, brominated biphenyl, and monobomobenzene may be cited. These reaction adjusting agents may be used either singly or in the form of a mixture of two or more members. It is particularly advantageous to use vinyl chloride or chlorinated ethylene among other reaction adjusting agents enumerated above. The concentration of the reaction adjusting agent is in the range of 0–1000 volume ppm, preferably 1–100 volume ppm, and particularly 1–50 volume %, based on the volume of the raw material gas. It has been ascertained to the inventors that the reaction adjusting agent, particularly vinyl chloride, which is used in this concentration serves the purpose of exalting the selectivity.

The temperature of the reaction vessel can be properly selected to suit the kind of unsaturated hydrocarbon having a chain length of 4–20 carbon atoms and containing no allylic hydrogen atom and used in the raw material gas. The temperature of the reaction vessel in operation is in the range of 150–300° C., preferably 170–250° C.

The spatial velocity of the raw material gas to be supplied to the interior of the reaction vessel is in the range of 100–30000 $hr^{-1}$, preferably 200–20000 $hr^1$. The reaction is only required to convert 0.1–75 mol %, preferably 1–60 mol %, and particularly preferably 1–50 mol %, of the unsaturated hydrocarbon having a chain length of 4–20 carbon atoms and containing no allylic hydrogen atom in the raw material. The unaltered portion of the unsaturated hydrocarbon having a chain length of 4–20 carbon atoms and containing no allylic hydrogen atom may be properly recycled to the reaction system. If the speed of supply of the raw material falls short of 100 $hr^{-1}$, the shortage will be at a disadvantage in degrading the efficiency of production. Conversely, if this speed exceeds 30000 $hr^{-1}$, the excess will be at a disadvantage in lowering the degree of conversion.

The actual retention time which is necessary for accomplishing the expected level of conversion may be varied in a wide range, depending on such factors as the kind of the raw material gas to be supplied, the ratio of the raw material gas to oxygen, the amount of a co-catalyst or a reaction accelerator to be deposited on the catalyst, the amount of silver deposited in the catalyst, and amount of the reaction adjusting agent present in the reaction gas, the temperature of the reaction, and the pressure of the reaction.

Now, the method for producing 3,4-epoxy-1-butene by catalytic vapor-phase oxidation of 1,3-butadiene with a oxygen-containing gas by the use of the catalyst described above will be explained below.

The reaction is performed by providing 1,3-butadiene, oxygen and optional organic halogenized compound, an oxygen/1,3-butadiene mol ratio controlling in the range of 0.01–20, further the organic halogenized compound being in the range of 0–1000 ppm by volume based on all of provided materials, preferably about 1–100 ppm. Optionally, gaseous inert dilution agent such as helium, nitrogen, argon and/or one or more mixture thereof may be used in the above-mentioned catalytic vapor-phase oxidation.

The organic halogen compound imposes no particular restriction and only requires to be capable of retaining a gaseous state in the reaction gas. As concrete examples of the organic halogen compound, methyl chloride, methyl bromide, dichloromethane, dibromomethane, ethyl chloride, ethyl bromide, dichloroethane, dibromoethane, vinyl chloride, dichloroethylene, dibromoethylene, trichloroethylene, dichloropropane, dibromopropane, dichloropropene, dibromopropene, chlorobutane, bromobutane, dichlorobutane, dibromobutane, and chlorobutene may be cited.

The reaction pressure may be changed extensively, although there is a limit of in the range of 0.01–10 MPa (gauge), preferably about 0.01–4 MPa (gauge), more preferably about 0.02–3 MPa (gauge).

The reaction time suitable for enforcement of the present invention may be changed extensively. The reaction can be carried out not only in single pass process but also in recycle process using outlet gas from the reactor. A method for single pass is described for the sake of convenience. Generally, 1,3-butadiene, oxygen, organic halogen compound and catalyst obtained by the present invention are retained for sufficient time such contact condition that a butadiene conversion is in the range of about 0.1–75 mol % by a single pass. The butadiene conversion is preferably in the range of about 1–50 mol % for efficient use of reactor vessel.

Contact time for achievement of desired conversion in the reaction may be changed extensively by depending on such factors as a ratio of 1,3-butadiene/oxygen, the amount of co-catalyst or stimulator deposited on the catalyst, the amount of silver deposited on the catalyst, the amount of organic halogen compound in the reaction gas, reaction temperature, reaction pressure and so on.

The space velocity is in the range of about 100–30,000 $hr^{-1}$, more preferably 200–20,000 $hr^{-1}$, and most preferably 300–10,000 $hr^{-1}$. The most suitable combination of butadiene convention and product selectivity thereby can be realized under these space velocity.

Experiments:

The present invention will be described more specifically below with reference to working examples. In Examples 1–11 and Controls 1–9 to be cited herein below, the relevant experiments were performed by packing the crushed catalyst in test tubes with a small inside diameter for demonstrating the effects thereof precisely and conveniently. The results of these experiments and the characters of carriers and catalyst used in every Example and Control are shown in Table 1–3.

The physical properties which are mentioned throughout the entire text of this specification represent the magnitudes which are determined by the following methods.

(1) Determination of $SiO_2$, $Na_2O$ and cationic components: These components are analyzed by X-ray fluorescence.

(2) Specific surface area: A carrier is crushed and sieved in 0.85–1.2 mm range. About 0.2 g of the sieved carrier particles is weighed accurately. After deaeration at 200° C. for at least 30 minutes, sample is measured for specific surface area by the B.E.T. (Brunauer-Emett-Teller) method.

(3) Average pore diameter: This property is measured by the mercury porosimeter.

(4) Water absorption rate: This property is determined as follows in due respect of the method of JIS R 2205-1998.

a) A non-crushed carrier (in the shape of pellets, rings or spheres, etc) is dried in an air oven until a constant mass was reached, and weighed (dry mass: $W_1$ (g)).

b) The weighed carrier is immersed in water, boiled in the water for more than 30 minutes, and then cooled in water kept at room temperature. The cooled carrier is used as a saturated sample.

c) The saturated sample is taken out from the water, quickly wiped with a damp cloth for removal of water drops, and then weighed (mass of saturated sample: $W_2$ (g)).

d) The water absorption is calculated in accordance with the following formula.

$$\text{Water absorption rate}(\%) = [(W_2-W_1)/W_1] \times 100$$

EXAMPLE 1

93 Mass parts of α-alumina (diameter of alumina crystal: 1 μm, average particle diameter: 40 μm, BET specific surface area: 2 m$^2$/g, sodium content (as reduced to Na): 16 mmol/kg) and 5 mass parts of methylcellulose were added into a kneader and mixed sufficiently. 4 Mass parts of aluminasol (as reduced to $Al_2O_3$) having particle diameter of 2–20 nm, 3 mass parts of colloidal-silica (as reduced $SiO_2$) having particle diameter of 2–20 nm, and 0.15 mass part of sodium hydroxide (as reduced to $Na_2O$) were added thereto, and mixed the resultant composition after adding 40 mass parts of water the composition. The carrier (Carrier A) was obtained by extrusion molding the resultant mixture, drying, calcining at the temperature of 1450° C. for 2 hours washing out with boiling water for 30 min of three times and drying thereof.

To a water slurry containing 30 g of silver oxalate placed in a beaker and kept cooled in a water bath, 16 ml of ethylenediamine was added to effect thorough solution of the silver compound. In this solution, 0.138 g of cesium chloride was dissolved completely. 100 Gram of carrier preheated in advance to 100° C. was placed in an evaporating dish setting on a boiling water bath, impregnated by adding silver containing solution to the carrier. After the silver containing solution was absorbed to the carrier, a heat treatment was performed in a hot oven with an air flow at 200°C. for 10 minutes and further at 400° C. for 10 minutes. Silver content of the obtained catalyst was 16.2 mass %, cesium content was 0.083 mass % based on the carrier as cesium atom.

The obtained silver-containing catalyst (Catalyst A1) was crushed and sieved in 0.85–1.2 mm in diameter. The sample was evaluated by the use of a single-pass flow reactor of cylinder type. The reaction tube is 40 cm in length, 10 mm in outside diameter, and 8 mm in inside diameter, was made of stainless steel and packed with a roll of quartz wool adapted to retain the catalyst at the center thereof. The reaction gas was composed of helium, 1,3-butadiene and oxygen whose volume ratio was controlled at 4:1:1 by means of a mass flow controller. Further, ethylenedichloride was added to the reaction gas in the range of 2–5 ppm by volume. The reaction for the oxidation of butadiene was carried out at a space velocity of 6,000 hr$^{-1}$ and a reaction temperature of 195° C. The reaction pressure (gauge) was controlled at 50 kPa. The feed gas and outlet gas form the reactor was analyzed by a thermal conduction detector with a capillary column (Pora PLOTQ: 0.53 mm in inside diameter, 50 m in length).

The gas chromatography was performed by retaining the oven temp at 115° C. for four minutes and then heating the oven to 230° C. at a temperature increasing rate of 7° C./min. Helium was used as the for the carrier gas chromatography.

EXAMPLE 2

A silver-containing catalyst (Catalyst A1) was obtained by following the procedure of Example 1 while using 0.159 g of cesium nitrate in the place of cesium chloride. Silver content of the catalyst obtained was 15.9 mass %, cesium content was 0.082 mass % as cesium atom.

EXAMPLE 3

A silver-containing catalyst (Catalyst A3) was obtained by following the procedure of Example 1 while using 0.217 g of thallium nitrate in place of cesium chloride. Silver content of the catalyst obtained was 15.9 mass %, thallium content was 0.128 mass % as thallium atom.

EXAMPLE 4

93 Mass parts of α-alumina (diameter of alumina crystal: 1 μm, average particle diameter: 65 μm, BET specific surface area: 3 m$^2$/g, sodium content (as reduced to Na): 16 mmol/kg) and 5 mass parts of sodium carboxymethyl cellulose salt were added into a kneader and mixed sufficiently. 4 Mass parts of aluminasol and 3 mass parts of colloidal-silica (as reduced to $SiO_2$) and 0.15 mass parts of sodium hydroxide (as reduced to Na) were added thereto, and mixed the resultant composition after adding 40 mass parts of water the composition. The carrier (Carrier B) was obtained by extrusion molding the resultant mixture, drying, calcining at the temperature of 1450° C. for 2 hours washing out with boiling water for 30 min of three times and drying thereof.

A silver-containing catalyst (Catalyst B1) was obtained by following the procedure of Example 1 while using a carrier B in stead of a carrier A and 0.244 g of cesium nitrate. Silver content of the catalyst obtained was 16.3 mass %, cesium content was 0.130 mass % as cesium atom.

EXAMPLE 5

A silver-containing catalyst (Catalyst B2) was obtained by following the procedure of Example 4 while using carrier B and using 0.325 g of cesium sulfate in place of cesium nitrate. Silver content of the catalyst obtained was 16.1 mass %, cesium content was 0.198 mass % as cesium atom.

EXAMPLE 6

93 Mass parts of α-alumina (diameter of alumina crystal: 0.5 μm, average particle diameter: 80 μm, BET specific surface area: 3 m$^2$/g, sodium content (as reduced to Na): 40 mmol/kg) and 5 mass parts of methyl cellulose were added into a kneader and mixed sufficiently. Four mass parts of aluminasol and 3 mass parts of colloidal-silica (as reduced to $SiO_2$) and 0.15 mass parts of sodium hydroxide (as reduced to Na) were added thereto, and mixed the resultant composition after adding 40 mass parts of water the composition. The carrier (Carrier C) was obtained by extrusion molding the resultant mixture, drying, calcining at the temperature of 1450° C. for 2 hours washing out with boiling water for 30 min of three times and drying thereof.

A silver-containing catalyst (Catalyst C) was obtained by following the procedure of Example 1 while using a carrier C and using 0.353 g of cesium nitrate. Silver content of the catalyst obtained was 15.7 mass %, cesium content was 0.196 mass % as cesium atom.

EXAMPLE 7

93 Mass parts of α-alumina (diameter of alumina crystal: 4 μm, average particle diameter: 40 μm, BET specific surface area: 1 $m^2/g$, sodium content (as reduced to Na): 8 mmol/kg) and 5 mass parts of sodium carboxymethyl cellulose salt were added into a kneader and mixed sufficiently. Four mass parts of aluminasol and 3 mass parts of colloidal-silica (as reduced to $SiO_2$) and 0.15 mass parts of sodium hydroxide (as reduced to Na) were added thereto, and mixed the resultant composition after adding 40 mass parts of water the composition. The carrier (Carrier D) was obtained by extrusion molding the resultant mixture, drying, calcining at the temperature of 1450 °C. for 2 hours washing out with boiling water for 30 min of three times and drying thereof.

A silver-containing catalyst (Catalyst D) was obtained by following the procedure of Example 1 while using a carrier D in place of a carrier A and using 0.121 g of cesium nitrate. Silver content of the catalyst obtained was 16.0 mass %, cesium content was 0.064 mass % as cesium atom.

EXAMPLE 8

84 Mass parts of α-alumina (diameter of alumina crystal: 3 μm, average particle diameter: 40 μm, BET specific surface area: 1 $m^2/g$, sodium content (as reduced to Na): 8 mmol/kg) and 10 mass parts of methyl cellulose were added into a kneader and mixed sufficiently. Four mass parts of aluminasol, 7 mass parts of colloidal-silica (as reduced to $SiO_2$) and 2.4 mass parts of sodium hydroxide (as reduced to Na) were added thereto, and mixed the resultant composition after adding 40 mass parts of water the composition. The carrier (Carrier E) was obtained by extrusion molding the resultant mixture, drying, calcining at the temperature of 1450° C. for 2 hours washing out with boiling water for 30 min of three times and drying thereof.

A silver-containing catalyst (Catalyst E) was obtained by following the procedure of Example 1 while using a carrier E in place of a carrier A and using 0.091 g of cesium nitrate instead. Silver content of the catalyst obtained was 15.8 mass %, cesium content was 0.053 mass % as cesium atom.

EXAMPLE 9

A silver-containing catalyst (Catalyst A4) was obtained by following the procedure of Example 1 while performing the heat treatment of the impregnated catalyst with superheated steam at 200° C. for 15 minutes. Silver content of the catalyst obtained was 16.1 mass %, cesium content-was 0.085 mass % as cesium atom.

EXAMPLE 10

To a water slurry containing 30 g of silver oxalate placed in a beaker and kept cooled in a water bath, 16 ml of ethylenediamine was added to effect thorough solution of the silver compound. In this solution, 0.81 g of cesium nitrate was dissolved completely. A hundred gram of carrier (carrier B) obtained by Example 4 and preheated in advance to 100° C. was placed in an evaporating dish setting on a boiling water bath, impregnated by adding silver containing solution to the carrier. After the silver containing solution was absorbed to the carrier, a heat treatment was performed in a hot oven with an air flow at 200° C. for 10 minutes and further at 400° C. for 10 minutes. Silver content of the obtained catalyst was 15.8 mass %, cesium content was 0.440 mass % based on the carrier as cesium atom.

Then, the obtained catalyst was filled up in a stainless steel hermetic container capable of introducing an inactive gas from the outside of container and placed in a tubular furnace. A catalyst was prepared by heat treatment at 565° C. for 3 hrs while supplying nitrogen gas.

The obtained silver-containing catalyst (Catalyst B3) was crushed and sieved in 0.85–1.2 mm in diameter. The sample was evaluated by the use of a single-pass flow reactor of cylinder type. The reaction tube is 40 cm in length, 9.53 mm in outside diameter, and 7.53 mm in inside diameter, was made of stainless steel and packed with a roll of quartz wool adapted to retain the catalyst at the center thereof. The reaction gas was composed of helium, 1,3-butadiene and oxygen whose volume ratio was controlled at 4:1:1 by means of a mass flow controller. Further, ethylenedichloride was added to the reaction gas in the range of 2–5 ppm by volume. The reaction for the oxidation of butadiene was carried out at a space velocity of 6,000 $hr^{-1}$ and a reaction temperature of 195° C. The reaction pressure (gauge) was controlled at 50 kPa. Analysis of raw material gas and resultant gas as well as gas chromatography were performed by the same manner of Example 1.

EXAMPLE 11

A silver-containing catalyst (Catalyst B4) was obtained by following the procedure of Example 10 while performing the heat treatment of the impregnated catalyst at 590° C. for 3 hours. The catalyst was used for Oxidation of 1,3-butadien. Silver content of the catalyst obtained was 15.8 mass %, cesium content was 0.482 mass % as cesium atom.

Control 1

A Catalyst was obtained (Catalyst A4) by following the procedure of Example 1 while omitting the use of an alkali metal. Silver content of the catalyst obtained was 15.9 mass %.

Control 2

93 Mass parts of α-alumina (diameter of alumina crystal: 0.5 μm, average particle diameter: 40 μm, BET specific surface area: 3 $m^2/g$, sodium content (as reduced to Na): 8 mmol/kg) and 5 mass parts of methyl cellulose were added into a kneader and mixed sufficiently. Four mass parts of aluminasol and 3 mass parts of colloidal-silica (as reduced to $SiO_2$) were added thereto, and mixed the resultant composition after adding 40 mass parts of water the composition. The carrier (Carrier F) was obtained by extrusion molding the resultant mixture, drying, calcining at the temperature of 1450° C. for 2 hours washing out with boiling water for 30 min of three times and drying thereof.

A Catalyst (Catalyst F) was obtained by following the procedure of Example 1 while using a carrier F as shown table 2 and using 0.338 g of cesium nitrate. Silver content of the catalyst obtained was 16.3 mass %, cesium content was 0.195 mass % as cesium atom.

Control 3

82 Mass parts of α-alumina (diameter of alumina crystal: 0.3 μm, average particle diameter: 5 μm, BET specific surface area: 10 m$^2$/g, sodium content (as reduced to Na): 16 mmol/kg ) and 10 mass parts of methyl cellulose were added into a kneader and mixed sufficiently. Four mass parts of aluminasol, 14 mass parts of colloidal-silica (as reduced to SiO$_2$) and 0.6 mass parts of sodium hydroxide (as reduced to Na) were added thereto, and mixed the resultant composition after adding 40 mass parts of water the composition. The carrier (Carrier G) was obtained by extrusion molding the resultant mixture, drying, calcining at the temperature of 1450° C. for 2 hours washing out with boiling water for 30 min of three times and drying thereof.

A Catalyst (Catalyst G) was obtained by following the procedure of Example 1 while using a carrier G and using 0.694 g of cesium nitrate. Silver content of the catalyst obtained was 15.7 mass %, cesium content was 0.393 mass % as cesium atom.

Control 4

93 Mass parts of α-alumina (diameter of alumina crystal: 0.5 μm, average particle diameter: 10 μm, BET specific surface area: 5 m$^2$/g, sodium content (as reduced to Na): 96 mmol/kg ) and 5 mass parts of methyl cellulose were added into a kneader and mixed sufficiently. Four mass parts of aluminasol, 3 mass parts of colloidal-silica (as reduced to SiO$_2$) and 3.5 mass parts of sodium hydroxide (as reduced to Na) were added thereto, and mixed the resultant composition after adding 40 mass parts of water the composition. The carrier (Carrier H) was obtained by extrusion molding the resultant mixture, drying, calcining at the temperature of 1450° C. for 2 hours washing out with boiling water for 30 min of three times and drying thereof.

A Catalyst (Catalyst H) was obtained by following the procedure of Example 1 while using a carrier H in place of a carrier A and using 0.148 g of cesium nitrate instead. Silver content of the catalyst obtained was 15.9 mass %, cesium content was 0.080 mass % as cesium atom.

Control 5

96 Mass parts of α-alumina (diameter of alumina crystal: 0.5 μm, average particle diameter: 30 μm, BET specific surface area: 2 m$^2$/g, sodium content (as reduced to Na): 0 mmol/kg) and 5 mass parts of methyl cellulose were added into a kneader and mixed sufficiently. Four mass parts of aluminasol was added thereto, and mixed the resultant composition after adding 40 mass parts of water the composition. The carrier (Carrier I) was obtained by extrusion molding the resultant mixture, drying, calcining at the temperature of 1450° C. for 2 hours washing out with boiling water for 30 min of three times and drying thereof.

A Catalyst (Catalyst I) was obtained by following the procedure of Example 1 while using a carrier I and using 0.200 g of cesium nitrate. Silver content of the catalyst obtained was 15.7 mass %, cesium content was 0.123 mass % as cesium atom.

Control 6

84 Mass parts of α-alumina (diameter of alumina crystal: 10 μm, average particle diameter: 60 μm, BET specific surface area: 1 m$^2$/g, sodium content (as reduced to Na): 8 mmol/kg ) and 5 mass parts of methyl cellulose were added into a kneader and mixed sufficiently. Four mass parts of aluminasol and 12 mass parts of colloidal-silica (as reduced to SiO$_2$) and 0.30 mass parts of sodium hydroxide (as reduced to Na) were added thereto, and mixed the resultant composition after adding 40 mass parts of water the composition. The carrier (Carrier J) was obtained by extrusion molding the resultant mixture, drying, calcining at the temperature of 1450° C. for 2 hours washing out with boiling water for 30 min of three times and drying thereof.

A catalyst (Catalyst J) was obtained by following the procedure of Example 1 while using a carrier J and using 0.093 g of cesium nitrate. Silver content of the catalyst obtained was 10.6 mass %, cesium content was 0.055 mass % as cesium atom.

Control 7

87 Mass parts of α-alumina (diameter of alumina if crystal: 20 μm, average particle diameter: 80 μm, BET specific surface area: 0.3 m$^2$/g, sodium content (as reduced to Na): 10 mmol/kg ) and 5 mass parts of methyl cellulose were added into a kneader and mixed sufficiently. Four mass parts of aluminasol and 9 mass parts of colloidal-silica (as reduced to SiO$_2$) and 0.30 mass parts of sodium hydroxide (as reduced to Na) were added thereto, and mixed the resultant composition after adding 40 mass parts of water the composition. The carrier (Carrier K) was obtained by extrusion molding the resultant mixture, drying, calcining at the temperature of 1450° C. for 2 hours washing out with boiling water for 30 min of three times and drying thereof.

A Catalyst (Catalyst K) was obtained by following the procedure of Example 1 while using a carrier K in place of a carrier A and using 0.014 g of cesium nitrate. Silver content of the catalyst obtained was 15.3 mass %, cesium content was 0.010 mass % as cesium atom.

Control 8

87 Mass parts of α-alumina (diameter of alumina crystal: 0.3 μm, average particle diameter: 5 μm, BET specific surface area: 10 m$^2$/g, sodium content (as reduced to Na): 16 mmol/kg ) and 5 mass parts of methyl cellulose were added into a kneader and mixed sufficiently. Four mass parts of aluminasol and 7 mass parts of colloidal-silica (as reduced to SiO$_2$) and 0.30 mass parts of sodium hydroxide (as reduced to Na) were added thereto, and mixed the resultant composition after adding 40 mass parts of water the composition. The carrier (Carrier L) was obtained by extrusion molding the resultant mixture, drying, calcining at the temperature of 1450° C. for 2 hours washing out with boiling water for 30 min of three times and drying thereof.

A Catalyst (Catalyst L) was obtained by following the procedure of Example 1 while using a carrier H in place of a carrier A and using 0.173 g of cesium nitrate instead. Silver content of the catalyst obtained was 15.9 mass %, cesium content was 0.622 mass % as cesium atom.

Control 9

84 Mass parts of α-alumina (diameter of alumina crystal: 0.8 μm, average particle diameter: 55 μm, BET specific surface area: 3 m$^2$/g, sodium content (as reduced to Na): 90 mmol/kg) and 5 mass parts of methyl cellulose were added into a kneader and mixed sufficiently. 4 Mass parts of aluminasol and 3 mass parts of colloidal-silica (as reduced to $SiO_2$) were added thereto, and mixed the resultant composition after adding 40 mass parts of water the composition. The carrier (Carrier M) was obtained by extrusion molding the resultant mixture, drying, calcining at the temperature of 1350° C. for 2 hours washing out with boiling water for 30 min of three times and drying thereof.

A Catalyst (Catalyst M) was obtained by following the procedure of Example 1 while using a carrier M in place of a carrier A and using 0.267 g of cesium nitrate instead. Silver content of the catalyst obtained was 15.8 mass %, cesium content was 0.090 mass % as cesium atom.

TABLE 1

| carrier | Specific Surface area ($m^2/g$) | $SiO_2$ (mass %) | $SiO_2$ per specific surface area (mass %/$m^2$) | $Na_2O$ (mass %) | $SiO_2/Na_2O$ | ave. pore diameter ($\mu m$) | Water apsorption rate (%) | vol, ratio of pores having a diameter of not more than 0.5$\mu$ (%) | vol, ratio of pores having a diameter of not more than 5$\mu$ (%) |
|---|---|---|---|---|---|---|---|---|---|
| A | 0.78 | 2.43 | 3.12 | 0.20 | 12 | 1.72 | 40 | 18 | 82 |
| B | 1.20 | 2.91 | 2.42 | 0.22 | 13 | 0.88 | 40 | 33 | 93 |
| C | 1.84 | 2.27 | 1.23 | 0.24 | 9 | 0.44 | 41 | 37 | 84 |
| D | 0.60 | 2.70 | 4.50 | 0.16 | 16 | 1.79 | 31 | 13 | 94 |
| E | 0.45 | 6.70 | 14.9 | 2.35 | 3 | 2.79 | 49 | 10 | 67 |
| F | 1.76 | 2.6 | 1.48 | 0.02 | 130 | 0.72 | 39 | 26 | 90 |
| G | 3.62 | 12.4 | 3.43 | 0.59 | 21 | 0.29 | 44 | 52 | 99 |
| H | 0.73 | 2.8 | 3.84 | 3.61 | 0.8 | 1.26 | 32 | 41 | 82 |
| I | 1.13 | 0.03 | 0.03 | 0.00 | — | 1.04 | 44 | 38 | 84 |
| J | 0.46 | 12.12 | 26.3 | 0.28 | 43 | 4.56 | 18 | 1 | 50 |
| K | 0.07 | 9.11 | 13.0 | 0.38 | 24 | 3.72 | 25 | 6 | 62 |
| L | 5.81 | 6.52 | 2.67 | 0.35 | 44 | 0.25 | 52 | 58 | 98 |
| M | 1.32 | 2.70 | 2.05 | 0.25 | 11 | 0.84 | 39 | 30 | 95 |

TABLE 2

| | characters of carriers | | | | mixing ratio for preparing carriers | | | | |
|---|---|---|---|---|---|---|---|---|---|
| carrier | Diameter of alumina crystal ($\mu m$) | Av. particle diameter ($\mu m$) | BET ($m^2/g$) | Sodium content (mmol/kg) | Amount of Alumina (mass parts) | Organic bainder (mass parts) | Aluminasol (mass parts) | Colloidal silica (mass parts) | Sodium hydroxide (mass parts) |
| A | 1 | 40 | 2 | 16 | 93 | 5(MC) | 4 | 3 | 0.15 |
| B | 1 | 65 | 3 | 16 | 93 | 5(CMC) | 4 | 3 | 0.15 |
| C | 0.5 | 80 | 3 | 40 | 93 | 5(MC) | 4 | 3 | 0.10 |
| D | 4 | 40 | 1 | 8 | 93 | 5(CMC) | 4 | 3 | 0.15 |
| E | 3 | 40 | 1 | 8 | 84 | 10(MC) | 4 | 7 | 2.4 |
| F | 0.5 | 40 | 3 | 8 | 93 | 5(MC) | 4 | 3 | 0 |
| G | 0.3 | 5 | 10 | 16 | 82 | 10(MC) | 4 | 14 | 0.6 |
| H | 0.5 | 10 | 5 | 96 | 93 | 5(MC) | 4 | 3 | 3.5 |
| I | 0.5 | 30 | 2 | 0.0 | 96 | 5(MC) | 4 | 0 | 0 |
| J | 10 | 60 | 1 | 8 | 84 | 5(MC) | 4 | 12 | 0.30 |
| K | 20 | 80 | 0.3 | 10 | 87 | 5(MC) | 4 | 9 | 0.30 |
| L | 0.3 | 5 | 10 | 16 | 89 | 5(MC) | 4 | 7 | 0.30 |
| M | 0.8 | 55 | 3 | 90 | 93 | 5(MC) | 4 | 3 | 0 |

MC: methylcellulose
CMC: carboxymethylcellulose sodium salt

TABLE 3

| | Catalyst | Carrier | silver content (mass %) | cation component Compound | Content (mass %) | reaction temp. (° C.) | reaction time for five hr C* (mol/%) | S** (mol/%) | one day after the reaction start C* (mol/%) | S** (mol/%) | 100 h after the reaction start C* (mol/%) | S** (mol/%) |
|---|---|---|---|---|---|---|---|---|---|---|---|---|
| Example 1 | A1 | A | 16.2 | CsCl | 0.083 | 195 | 16 | 92 | 16 | 92 | | |
| Example 2 | A2 | A | 15.9 | $CsNO_3$ | 0.082 | 195 | 19 | 93 | 19 | 93 | | |
| Example 3 | A3 | A | 15.9 | $TlNO_3$ | 0.128 | 195 | 15 | 91 | 13 | 92 | | |
| Example 4 | B1 | B | 16.3 | $CsNO_3$ | 0.130 | 195 | 17 | 93 | 16 | 93 | | |
| Example 5 | B2 | B | 16.1 | $Cs_2SO_4$ | 0.198 | 195 | 13 | 93 | 12 | 92 | | |
| Example 6 | C | C | 15.7 | $CsNO_3$ | 0.196 | 195 | 18 | 92 | 16 | 91 | | |
| Example 7 | D | D | 16.0 | $CsNO_3$ | 0.064 | 195 | 12 | 90 | 11 | 90 | | |
| Example 8 | E | E | 15.8 | $CsNO_3$ | 0.053 | 195 | 7 | 89 | 7 | 89 | | |
| Example 9 | A4 | A | 16.1 | CsCl | 0.085 | 195 | 12 | 92 | 11 | 91 | | |
| Example 10 | B3 | B | 15.8 | $CsNO_3$ | 0.440 | 195 | 17 | 89 | 17 | 90 | 16 | 90 |
| Example 11 | B4 | B | 16.3 | $CsNO_3$ | 0.482 | 195 | 14 | 87 | 15 | 88 | 13 | 87 |
| Control 1 | A5 | A | 15.9 | — | — | 195 | 0.2 | 78 | almost no reaction | | | |
| Control 2 | F | F | 16.3 | $CsNO_3$ | 0.195 | 195 | 5 | 74 | almost no reaction | | | |

TABLE 3-continued

| | | | silver content | cation component | | reaction temp. | reaction time for five hr | | one day after the reaction start | | 100 h after the reaction start | |
|---|---|---|---|---|---|---|---|---|---|---|---|---|
| | Catalyst | Carrier | (mass %) | Compound | Content (mass %) | (° C.) | C* (mol/%) | S** (mol/%) | C* (mol/%) | S** (mol/%) | C* (mol/%) | S** (mol/%) |
| Control 3 | G | G | 15.7 | CsNO$_3$ | 0.393 | 195 | 4 | 75 | almost no reaction | | | |
| Control 4 | H | H | 15.9 | CsNO$_3$ | 0.080 | 195 | almost no reaction | | | | | |
| Control 5 | I | I | 15.7 | CsCl | 0.123 | 195 | almost no reaction | | | | | |
| Control 6 | J | J | 10.6 | CsNO$_3$ | 0.055 | 195 | 2 | 82 | | | | |
| Control 7 | K | K | 15.3 | CsNO$_3$ | 0.010 | 195 | almost no reaction | | | | | |
| Control 8 | L | L | 15.9 | CsNO$_3$ | 0.622 | 195 | almost no reaction | | | | | |
| Control 9 | M | M | 15.8 | CsNO$_3$ | 0.090 | 195 | 6 | 84 | 0.9 | 82 | | |

C*conversion ratio
S**Selectivity ratio

The entire disclosure of Japanese Patent Application No.11-267467 filed on Sep. 21, 1999 including specification, claims, drawing and summary are incorporated herein by reference in its entirety.

What is claimed is:

1. A method for the production of epoxides, said method comprising vapor-phase oxidation of an unsaturated hydrocarbon having a chain length of 4–20 carbon atoms and containing no allylic hydrogen atom with a molecular oxygen-containing gas in the presence of a catalyst, wherein said catalyst is characterized by having a catalytic component containing silver and at least one element selected from the group consisting of alkali metals and thallium deposited onto a carrier obtained by mixing α-alumina having a sodium content in the range of 1–70 mmol (as reduced to Na) per kg of α-alumina with an aluminium compound, a silicon compound, and a sodium compound and calcining the resultant mixture, the carrier having a silicon content (as reduced to SiO$_2$) in the range of 0.3–11.0 mass % based on the mass of the carrier and a sodium content (as reduced to Na$_2$O) in the range of 0.11–2.5 mass % based on the mass of the carrier, wherein a volume ratio of pores having diameters of not more than 0.5 μm is not more than 50%, and not more than 5 μm is more than 65%, based on the carrier.

2. A method for the production of 3,4-epoxy-1-butene, said method comprising vapor-phase oxidation of 1,3-butadiene with a molecular oxygen-containing gas in the presence of a catalyst, wherein said catalyst is characterized by having a catalytic component containing silver and at least one element selected from the group consisting of alkali metals and thallium deposited onto a carrier obtained by mixing α-alumina having a sodium content in the range of 1–70 mmol (as reduced to Na) per kg of α-alumina with an aluminium compound, a silicon compound, and a sodium compound and calcining the resultant mixture, the carrier having a silicon content (as reduced to SiO$_2$) in the range of 0.3–11.0 mass % based on the mass of the carrier and a sodium content (as reduced to Na$_2$O) in the range of 0.11–2.5 mass % based on the mass of the carrier, wherein a volume ratio of pores having diameters of not more than 0.5 μm is not more than 50%, and not more than 5 μm is more than 65%, based on the carrier.

3. A method according to claim 1, wherein said carrier has a specific surface area in the range of 0.1–5 m$^2$/g based on the mass of the carrier, a water absorption ratio in the range of 20–50%, and an average pore diameter in the range of 0.3–3.5 μm.

4. A method according to claim 1, wherein the mass ratio of silicon to sodium compound in said catalyst (SiO$_2$/Na$_2$O) is in the range of 1–20.

5. A method according to claim 1, wherein said a silicon content of said carrier per-unit surface area is in the range of 0.1–20 mass %/(m$^2$/g) based on the mass of said carrier.

6. A method according to claim 1, which contains silver as a catalytic component in the range of 5–25% by mass and at least one element selected from the group consisting of alkali metals and thallium in the range of 0.001–5% by mass, based on the total mass of the catalyst.

7. A method according to claim 1, wherein a catalyst component containing silver and at least one element selected from the group containing of alkali metals and thallium is deposited on said carrier and thereafter the resultant composite is eventually heat-treated in an inert gas containing substantially no oxygen at an elevated temperature in the range of 400–700° C.

8. A method according to claim 2, wherein said carrier has a specific surface area in the range of 0.1–5 m$^2$/g based on the mass of the carrier, a water absorption ratio in the range of 20–50%, and an average pore diameter in the range of 0.3–3.5 μm.

9. A method according to claim 2, wherein the mass ratio of silicon to sodium compound in said catalyst (SiO$_2$/Na$_2$O) is in the range of 1–20.

10. A method according to claim 2, wherein said a silicon content of said carrier per unit surface area is in the range of 0.1–20 mass %/(m$^2$/g) based on the mass of said carrier.

11. A method according to claim 2, which contains silver as a catalytic component in the range of 5–25% by mass and at least one element selected from the group consisting of alkali metals and thallium in the range of 0.001–5% by mass, based on the total mass of the catalyst.

12. A method according to claim 2, wherein a catalyst component containing silver and at least one element selected from the group containing of alkali metals and thallium is deposited on said carrier and thereafter the resultant composite is eventually heat-treated in an inert gas containing substantially no oxygen at an elevated temperature in the range of 400–700° C.

* * * * *